United States Patent [19]

Gillespie

[11] Patent Number: 5,137,718
[45] Date of Patent: Aug. 11, 1992

[54] INFECTION FIGHTING COMPOSITION FOR TOPICAL APPLICATION

[75] Inventor: C. Edward Gillespie, Goldsboro, N.C.

[73] Assignee: G&S Medical Ltd, Goldsboro, N.C.

[21] Appl. No.: 523,669

[22] Filed: May 15, 1990

[51] Int. Cl.$^5$ ............ A61K 31/74; A61K 31/79; A01N 25/08; C08B 11/08
[52] U.S. Cl. .............................. 424/78.24; 424/78.01; 424/78.07; 424/78.25; 424/405; 424/409; 424/443; 424/445; 424/447; 424/449; 424/484; 424/488; 424/667; 424/672; 514/772.1; 514/781; 514/887; 514/772.3; 536/84; 536/96
[58] Field of Search .............. 424/78, 80, 405, 409, 424/443, 445, 447, 449, 484, 488, 667, 672, 78.01, 78.07, 78.24, 78.25; 514/873, 886, 887, 944, 772.1, 772.3, 781, 953, 964, 965; 536/84, 96

[56] References Cited

U.S. PATENT DOCUMENTS 4,364,929 12/1982 Sasmor et al. ............... 424/80

FOREIGN PATENT DOCUMENTS 2438594 8/1974 Fed. Rep. of Germany ........ 424/80
2553683 12/1974 Fed. Rep. of Germany ........ 424/80
2557607 12/1974 Fed. Rep. of Germany ........ 424/80

*Primary Examiner*—Thurman K. Page
*Assistant Examiner*—Carlos Azpuru
*Attorney, Agent, or Firm*—Francis T. Kremblas, Jr.

[57] ABSTRACT

A composition for a topically applied therapeutic cream or ointment having effective activity against one or a combination of sources of viral, bacterial, yeast and fungus infections characterized by the ability to penetrate beneath the epidermal layer of the skin. The composition includes a water soluble active component which is formulated with a water soluble organic solid base and a water soluble surfactant to form an aqueous solution having a gel-like consistency. A preferred active ingredient is a povidone-iodine complex. A preferred carrier is hydroxyethylcellulose.

5 Claims, No Drawings

INFECTION FIGHTING COMPOSITION FOR TOPICAL APPLICATION

BACKGROUND ART

Conventional topical creams and ointments carrying an active viricidal or microbicidal agent have employed a water-oil emulsion type formulation. Some of the disadvantages of such prior formulations are related to their greasy feeling, or the clothes staining ability, or to the ease in which they are inadvertently wiped off the affected area. The latter trait tends to decrease their effectiveness and the former traits tend to discourage users from using the same as often as medically advantageous.

A very important disadvantage in these prior art formulations is their effectiveness extends essentially only to the surface of the epidermis, except for any small portion which may contact an open wound or sore on the skin. These prior art formulations have very limited ability to penetrate through the pores of the epidermal layer to contact an infectious agent located below the surface of the epidermis.

Another disadvantage of prior oil/water emulsion type compositions, particularly with certain active agents such as povidone-iodine, is shorter shelf life. That is, the composition tends to separate or lose its homogenous character or interact with the active agent and decrease its intended effectiveness.

Therefore, prior to the present invention, there has been an unfulfilled need for a topical cream or ointment type composition carrying an active viricide and/or microbicide or the like, which does not possess the disadvantages noted above and which has the ability to deliver an effective concentration of the active ingredient to both the immediate surface area and penetrate beneath the surface area of the skin to enhance effectiveness of the active agent.

SUMMARY OF INVENTION

The present invention relates generally to compositions for topically applied pharmaceutical creams or ointments effective against infectious agents, and particularly to a novel composition which possesses increased effectiveness and eliminates many of the undesirable characteristics associated with prior art compositions used for this purpose.

A composition of the present invention for topical application of an active agent effective against infectious sources, includes a solution of a water soluble form of an active ingredient, a surfactant and a solid, water soluble, carrier forming a gel-like consistency and viscosity suitable for the intended use. A used herein, the term gel-like is used to refer to a material which has a consistency similar to creams and ointments within the viscosity range later described herein.

The viscosity of the composition formed is preferably in the range of about 8000 to 15,000 cps at 25 degrees C. A more preferable viscosity range is between 8500 to 11,500 cps at 25 degrees C. The carrier or base functions not only to form an aqueous solution with the active agent and a surfactant, but further acts as a stabilizer to permit an effective amount of the composition to be applied by gentle massage to a reasonably specific area of the skin. It is also important that the water-soluble carrier does not react with the active ingredient in solution to negate or minimize the effectiveness of the active ingredient or to cause a precipitate to form in the presence of the other components.

In a preferred embodiment of the present invention disclosed herein, the preferred active ingredient is a polyvinylpyrrolidone-iodine complex, commonly known as povidone-iodine, a well-known agent having viricidal and microbicidal effectiveness. A preferred suitable water soluble surfactant is a nonyphenoxy-poly-(etheneoxy) ethanol. An emollient, such as glycerin is added to reduce any irritating effect of the iodine. A conventional pharmaceutically acceptable defoamer is included to reduce foaming during the mixing process.

One aspect of the present invention is to provide a composition which functions as an efficient delivery system of the anti-infection active ingredient for topical application to the skin.

As another aspect of the present invention, water soluble components are employed in a manner to provide a viscous aqueous solution which does not leave a greasy residue nor easily stain the clothes of the user.

In another aspect of the composition of the present invention, a water soluble solution is provided in a relatively viscous form which possesses the capability to penetrate through the skin pores in the epidermis to deliver an effective concentration of the active ingredient beneath the surface of the skin. This characteristic provides longer lasting effectiveness and reaches infectious agents which are located below the surface layer of the skin.

As a further advantage of the present invention, the water soluble carrier in the composition functions to lengthen the effective shelf life of the composition as compared to the prior art oil/water emulsion compositions, particularly when povidone-iodine is used as the active agent.

As a further advantage of the present invention, an active ingredient, such as a povidone-iodine complex, which has a wide range effectiveness against viruses, fungi, yeast and bacteria can be formulated into a convenient, highly effective cream or gel-like form which is easily topically applied to an area subject to contact with infectious agents, or an area having an existing infection.

In describing the preferred embodiment of the invention, specific terminology will be resorted to for the sake of clarity. However, it is not intended that the invention be limited to the specific terms so selected and it is to be understood that each specific term includes all technical equivalents which operate in a similar manner to accomplish a similar purpose within the context of the present invention.

DETAILED DESCRIPTION

The present invention relates to an improved composition for topically applied infection fighting agents which includes a novel water soluble carrier capable of forming a viscous gel-like solution particularly suitable for application to the skin.

Unlike prior art oil/water emulsion compositions, the water soluble composition of the present invention is easily massaged into the skin to provide an effective concentration of the active ingredient to the epidermal surface area of the skin and to areas beneath the epidermal layer.

In the preferred embodiment disclosed herein, a povidone-iodine complex is used as the active ingredient. Iodine is well-known to be effective to kill viruses, bacteria, yeasts and fungi. A povidone-iodine complex has long been used to provide a longer sustained release of an effective concentration of iodine. However, unlike prior topical formulations used for this purpose, the povidone-iodine complex is mixed in solution with a water soluble carrier in accordance with the present invention to form a gel-like base. The preferred novel water soluble carrier is hydroxyethylcellulose.

The hydroxyethylcellulose, in powder form, is added to a selected aqueous solution of povidone-iodine until the viscosity approaches a cream or gel-like consistency suitable for massaging into the skin. A pharmaceutically acceptable, water soluble surfactant is also included to reduce surface tension and aid the ability of the composition to penetrate through the pores of the epidermal layer, thereby delivering an effective concentration of povidone-iodine beneath the surface of the skin.

A preferred surfactant is a nonyphenoxy-poly-(etheneoxy) ethanol, such as IGEPAL CO-660 commercially available from GAF Corporation.

An emollient is also included to reduce the irritating effective of iodine on healthy tissue. A preferred emollient is glycerin which is miscible in water.

The order in which the components are mixed is important. The selected quantity of the povidone-iodine complex and the relatively small quantities of the surfactant and the soluble or miscible emollient are mixed in the selected amount of water. A conventional defoamer may be added to reduce the tendency of foaming during the mixing process. Then, the selected amount of water soluble carrier is carefully added into and mixed with the aqueous solution of the other components and allowed to hydrolyze. The resulting product is a creamy gel-like product having the desired viscosity.

This resulting composition is an homogenous, aqueous solution of all the components used. The stability of the solution significantly improves the shelf life of the composition compared to the prior art oil/water emulsion type composition.

The prior art formulations of products of the type described herein using oil/water emulsions tend to clog the pores of the skin. Therefore they are essentially limited to activity on the surface of the skin. However, using a relative small amount of surfactant in the composition of the present invention is sufficient to reduce surface tension to readily allow the water soluble composition to penetrate more deeply into the epidermis and likely to extend into the dermal layer of the skin.

As mentioned earlier herein, this feature provides the added advantage of increasing the length of time of effectiveness of the infection fighting active ingredient as well as provide effectiveness against infectious agents already present under the surface of the epidermis.

To applicant's knowledge, no prior topical applied cream or ointment carrying an active ingredient effective against infectious agents has employed this improved delivery system. Conventional wisdom prior to the present invention has employed only the oil/water emulsion type formulations which possess the disadvantages noted herein.

Povidone-iodine, prior to the present invention, has been principally limited to antiseptic type uses, however its wide ranging effectiveness against most infectious type agents is well-known. It is often employed in hospital settings as a soap scrub prior to surgery or as a low viscosity fluid rinse in surgical cavities because of this effectiveness.

However, employing povidone-iodine with the novel carrier system of the present invention permits this highly effective agent to be more efficiently used in a topical cream or gel-like form in a dramatically wider range of applications wherein it can be stabilized and massaged gently into the intended area of application.

It has effectiveness in killing viruses, such as the herpes virus; fungus, such as commonly encountered in athlete's foot disease; and a wide range of gram positive and gram negative bacteria. It also is effective against yeast and protozoa infections. Therefore, in a non-greasy cream-type composition, this highly effective ingredient can be conveniently topically applied to an infected area and deliver effective concentrations of povidone-iodine on the surface of the epidermis as well as penetrate beneath the surface. This results in longer and improved effectiveness.

Further, the non-greasy nature of the composition of the present invention lends itself to use as a preventative antiseptic in certain high risk situations. For example, hospital and emergency personnel, frequently exposed to blood or other body fluids in their occupation, may massage the composition of the present invention on their hands prior to donning the typical protective gloves.

The non-greasy characteristics minimizes the excessive slippery feeling to the user wearing such gloves as compared to the prior art water-oil emulsions. Further, the longer period of effectiveness described herein provides significantly enhanced protection against infectious agents which inadvertently may pass through a flaw in the gloves of the user.

Presently, an on-going testing program in several major college athletic programs is directed to well known fungus infections, commonly referred to as athlete's foot and jock itch. Preliminary results have been highly favorable using the composition of the present invention as the primary treatment of these diseases.

In view of prior published reports of the effectiveness of povidone-iodine regarding the herpes virus, clinical tests concerning diseases caused by this virus are expected to show highly beneficial results employing the preferred composition disclosed herein in a convenient and more effective form for topical applications.

The following example describes a preferred embodiment of the composition of the present invention and the method of formulatinq the same.

EXAMPLE I

The components were prepared in amounts as specified in Table I set forth below and added in the following sequence. First, a commercially available povidone-iodine complex complying with current U.S.P. standards was dissolved in a selected amount of deionized water in a suitable mixing vessel. Then the selected amount of disodium phosphate was dissolved in a predetermined amount of hot deionized water and the solution added to the povidone-iodine solution to adjust the pH to a value between about 4.to 4.5. Next a water solution containing the specified amount of a conventional defoamer was added to the solution in the container which was followed by adding the specified amounts of glycerin and surfactant to the mixing vessel. The contents of the vessel were thoroughly stirred to assure a homogenous solution was formed. Deionized water is added as needed to adjust the water content to meet the amount specified such as the value shown below in Table I. Then hydroxyethylcellulose powder is sprinkled into the solution with stirring until the specified amount has been added. The resulting composition is a clear, brown colored gel-like cream having a viscosity of between 8500 to 11,500 cps at 25 degrees C. and a specific gravity of between 1.038 to 1.046 at 25 degrees C.

It is important that the hyroxyethylcellulose base is added after the other components are thoroughly dissolved into solution. If the base is added prior to the addition of the other components, a homogeneous solution of the other components is not likely while keeping the viscosity in the desired range for final product.

A list of the components of a preferred composition of the present invention expressed by weight in pounds is shown in Table I. All of the components meet current U.S. Patent standards for human use.

TABLE I

| Components | | LBS. |
| --- | --- | --- |
| Active Agent | Povidone-Iodine | 10.35 |
| pH adjuster | Disodium Phosphate | 0.53 |
| Defoamer | Methysiloxane | 0.033 |
| Surfactant | Nonylphenoxy-poly-(etheneoxy) ethanol | 0.24 |
| Emollient | Glycerin | 0.24 |
| Base | Hydroxyethylcellulose | 1.41 |
| | Deionized Water (total) | 87.0 |

The surfactant used is known as IGEPAL CO-660 available from the GAF Corporation. The defoamer is a methysiloxane available from DOW Corporation under the trade name Mazu DF2105. The hydroxyethylcellulose base is known under the trade name Natrosol 250HR.

Hydroxyethylcellulose is particularly compatible with an active ingredient such as the povidone-iodine complex in that it remains in solution without precipitating over long period of shelf storage. This is particularly important for topical compositions for the intended use of the present invention. If the composition loses its homogenous character by precipitation or if the base should react with the active ingredient to form a different compound, the delivery of the appropriate concentration of the active ingredient to fight infectious agents may be seriously impaired.

Further, if any solids are present in the composition, their presence tends to clog the pores. Then penetration of the composition through the pores of the skin is impaired.

For example, hydroxymethylcellulose proved to be a less desirable base because it tends to precipitate out of solution in the presence of iodine. Therefore the particular water soluble base must be appropriately compatible with the other components, and particularly the active agent, to avoid the loss of this important feature of the composition of the present invention.

Additionally, the pH of the composition should be adjusted within a specified range matched to the area of application. For example, for topical applications to the epidermis, a pH of about 4.0 to 4.5 works well. However, for applications related to vaginal uses, a pH in the range of about 1.75 to 2.1 is more appropriate.

While certain preferred embodiments of the present invention have been disclosed in detail, it is to be understood that various modifications may be adopted without departing from the spirit of the invention or scope of the following claims.

I claim:

1. An improved topically applied therapeutic agent comprising, in combination;
    a) a povidone-iodine complex and hydroxyethylcellulose in a weight percent ratio greater than 3 parts of a povidone-iodine complex to each part of hydroxyethylcellulose to provide an effective therapeutic amount of iodine for topical applications;
    b) a water soluble surfactant in an amount effective to aid penetration of the composition through the pores of the epidermal layer of a human;
    c) an emollient in an amount effective to reduce the irritating effect of iodine on healthy human tissue; and
    d) water in an amount effective to form a homogeneous solution of the components in (a), (b) and (c) having a gel-like consistency which does not result in stratification into separate layers and a viscosity in a range between 8000 to 15,000 cps at 25 degrees C.

2. The composition defined in claim 1 having the ability to penetrate through the pores of the human epidermis layer upon topical application.

3. The composition defined in claim 2 wherein said weight percent ratio between the povidone-iodine complex and the hydroxyethylcellulose is at least 6 to 1 or greater.

4. A method of making a water soluble topical ointment therapeutically effective against one or a combination of sources of viral, bacterial, yeast or fungus infections, comprising the steps of:
    a) forming an aqueous solution containing a selected amount of a povidone-iodine complex in a selected amount of water;
    b) adding a water-soluble emollient to the solution formed in step (a);
    c) adding an amount of hydroxyethylcellulose to said solution containing the components in (a), (b) and (c) effective to form a gel-like consistency which does not result in stratification into separate layers and which has a viscosity between about 8000 to 15,000 cps at 25 degrees C., wherein the weight percent ratio of said povidone-iodine complex to said amount of hydroxyethylcellulose added is greater than 3 to 1.

5. The method defined in claim 4 wherein said weight percent ratio of said povidone-iodine complex to said hydroxyethylcellulose is at least 6 to 1.

* * * * *